US00PP19037P2

(12) United States Plant Patent
Houbraken

(10) Patent No.: US PP19,037 P2
(45) Date of Patent: Jul. 22, 2008

(54) ***ARGYRANTHEMUM* PLANT NAMED 'ARGYWHIMI'**

(50) Latin Name: *Argyranthemum frutescens*
Varietal Denomination: Argywhimi

(75) Inventor: Anna M. W. P. Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 324 days.

(21) Appl. No.: 11/223,870

(22) Filed: Sep. 8, 2005

(51) Int. Cl.
*A01H 5/00* (2006.01)

(52) U.S. Cl. ..... Plt./406
(58) Field of Classification Search ..... Plt./406, Plt./263
See application file for complete search history.

(56) References Cited

PUBLICATIONS

UPOV PBR 20031832 filed October 13, 2003.*

* cited by examiner

*Primary Examiner*—Anne Marie Grunberg
*Assistant Examiner*—Louanne Krawczewicz Myers
(74) *Attorney, Agent, or Firm*—C. A. Whealy

(57) ABSTRACT

A new and distinct cultivar of *Argyranthemum* plant named 'Argywhimi', characterized by its compact, upright and rounded plant habit; freely branching habit and short internodes; dense and bushy plant habit; early flowering habit; freely flowering habit with numerous inflorescences per plant; and daisy-type inflorescences with white-colored ray florets and golden yellow-colored disc florets.

1 Drawing Sheet

Botanical designation: *Argyranthemum frutescens.*
Cultivar denomination: 'Argywhimi'.

BACKGROUND OF THE INVENTION

The present invention relates to a new and distinct cultivar of *Argyranthemum* plant, botanically known as *Argyranthemum frutescens* and hereinafter referred to by the cultivar name 'Argywhimi'.

The new *Argyranthemum* is a product of a planned breeding program conducted by the Inventor in Enkhuizen, The Netherlands. The objective of the breeding program was to create new compact *Argyranthemums* with early and freely flowering habit.

The new *Argyranthemum* originated from a open-pollination conducted in Enkhuizen, The Netherlands in 1999 of a proprietary selection of *Argyranthemum frutescens* identified as code number B 6-3, not patented, as the female, or seed, parent with an unknown selection of *Argyranthemum frutescens* as the male, or pollen, parent. The cultivar Argywhimi was discovered and selected by the Inventor as a single plant within the progeny of the stated open-pollination in a controlled environment in Enkhuizen, The Netherlands in August, 2000.

Asexual reproduction of the new *Argyranthemum* by terminal cuttings in a controlled environment in Enkhuizen, The Netherlands since August, 2000, has shown that the unique features of this new *Argyranthemum* are stable and reproduced true to type in successive generations.

SUMMARY OF THE INVENTION

The new *Argyranthemum* has not been observed under all possible environmental conditions. The phenotype may vary somewhat with variations in environment such as temperature and light intensity without, however, any variance in genotype.

The following characteristics have been repeatedly observed and are determined to be basic characteristics of 'Argywhimi' and distinguish the new *Argyranthemum* as a new and distinct cultivar:

1. Compact, upright and rounded plant habit.
2. Freely branching habit and short internodes; dense and bushy plant habit.
3. Early flowering habit.
4. Freely flowering habit with numerous inflorescences per plant.
5. Daisy-type inflorescences with white-colored ray florets and golden yellow-colored disc florets.

Plants of the new *Argyranthemum* differ from plants of the female parent selection in the following characteristics:

1. Plants of the new *Argyranthemum* are more vigorous and stronger than plants of the female parent selection.
2. Plants of the new *Argyranthemum* have darker green-colored foliage than plants of the female parent selection.
3. Plants of the new *Argyranthemum* have larger inflorescences than plants of the female parent selection.

Plants of the new *Argyranthemum* can be compared to plants of the cultivar Innpetita, not patented. In side-by-side comparisons conducted in Enkhuizen, The Netherlands, plants of the new *Argyranthemum* differed from plants of the cultivar Innpetita in the following characteristics:

1. Plants of the new *Argyranthemum* were smaller than plants of the cultivar Innpetita.
2. Plants of the new *Argyranthemum* were more freely branching than plants of the cultivar Innpetita.

3. Plants of the new *Argyranthemum* had smaller inflorescences than plants of the cultivar Innpetita.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Argyranthemum.*

The photograph at the bottom of the sheet comprises a side perspective view of a typical flowering plant of 'Argywhimi' grown in a container.

The photographs at the top of the sheet comprise close-up views of typical inflorescences of 'Argywhimi'.

DETAILED BOTANICAL DESCRIPTION

The aforementioned photographs, following observations and averaged measurements describe plants grown in Gilroy, Calif., in an outdoor nursery under full sunlight during the summer with day temperatures ranging from 18° C. to 39° C. and night temperatures ranging from 10° C. to 17° C. Plants of grown in one-gallon containers. Plants had been growing for about 18 weeks when the photographs and description were taken. Color references are made to The Royal Horticultural Society Colour Chart, 1995 Edition, except where general terms of ordinary dictionary significance are used.

Botanical classification: *Argyranthemum frutescens* cultivar Argywhimi.

Parentage:

*Female, or seed, parent.*—Proprietary selection of *Argyranthemum frutescens* identified as code number B 6-3, not patented.

*Male, or pollen, parent.*—Unknown selection of *Argyranthemum frutescens,* not patented.

Propagation:

*Type.*—Terminal vegetative cuttings.

*Time to initiate roots.*—About 7 to 10 days at 21° C.

*Time to produce a rooted cutting.*—About 14 to 20 days at 20° C.

*Root description.*—Fibrous, relatively fine; white in color.

*Rooting description.*—Freely branching; dense.

Plant description:

*General appearance.*—Inverted triangle; compact, upright and rounded plant form with dense foliage, short internodes and inflorescences held above and beyond the foliage; dense and bushy plant habit. Moderately vigorous growth habit.

*Plant height.*—About 26 cm.

*Plant width.*—About 41 cm.

*Lateral branch description.*—Quantity per plant: Freely branching with about 18 primary lateral branches each with about five or six secondary lateral branches. Length: About 24 cm. Diameter: About 7 mm. Internode length: Short, about 1.5 cm to 2 cm. Aspect: Initially upright to outwardly spreading. Texture: Smooth, glabrous. Strength: Very strong. Color: Developing stems, 145B; older stems, 145B with tiny specks, 183A in color.

*Foliage description.*—Arrangement: Alternate, simple. Length: About 2.3 cm. Width: About 2.5 cm. Shape: Tri-lobed, deeply dissected. Apex: Broadly acute. Base: Attenuate, clasping. Margin: Deeply dissected; serrated. Texture, upper and lower surfaces: Smooth, glabrous. Venation pattern: Pinnate. Petiole length: About 1.5 cm. Petiole diameter: About 3 mm. Petiole texture, upper and lower surfaces: Smooth, glabrous. Color: Developing foliage, upper and lower surfaces: 137A. Fully expanded foliage, upper surface: Slightly darker than 137A; venation, 137A. Fully expanded foliage, lower surface: 137A; venation, 147A. Petiole, upper and lower surfaces: 137B.

Inflorescence description:

*Appearance.*—Daisy-type inflorescences with ligulate ray florets. Disc and ray florets develop acropetally on a capitulum. Inflorescences held upright and outwardly on terminal and axillary peduncles. Inflorescences positioned perpendicular to the peduncles. Inflorescences persistent.

*Flowering response.*—Under natural conditions, plant flower from spring to early fall in California; plants flower continuous during this period. Early flowering habit, plants being flowering about 10 to 12 weeks after planting.

*Inflorescence longevity.*—Inflorescences last about ten days on the plant.

*Quantity of inflorescences.*—Freely flowering, about 800 open inflorescences and inflorescence buds per plant.

*Fragrance.*—Like sour milk.

*Inflorescence size.*—Diameter: About 2.5 cm. Depth (height): About 8 mm. Diameter of disc: About 1 cm. Receptacle height: About 6 mm. Receptacle diameter: About 9 mm.

*Inflorescence buds.*—Height: About 9 mm. Diameter: About 6 mm. Shape: Ovoid. Color: 155D.

*Ray florets.*—Quantity per inflorescence: About 16 to 18 arranged in a single whorl. Shape: Ligulate. Length: About 1 cm. Width: About 4 mm. Apex: Emarginate. Base: Attenuate. Margin: Entire. Texture, upper and lower surfaces: Smooth, glabrous; longitudinally ridged. Aspect: initially upright; with development, eventually close to perpendicular to the peduncle. Color: When opening, upper surface: 155B. When opening, lower surface: 155D. Fully opened, upper surface: Whiter than 155D. Fully opened, lower surface: 155D.

*Disc florets.*—Arrangement: Massed at the center of the inflorescence. Quantity per inflorescence: Numerous, about 94. Shape: Tubular, elongated; apex, five-pointed; base, fused. Length: About 5 mm. Diameter, apex: About 1.5 mm. Diameter, base: Less than 1 mm. Color: Immature: 13A. Mature, apex and mid-section: 14A. Mature, base: 145A.

*Involucral bracts (phyllaries).*—Appearance: Scale-like; margins, papery and membranous. Quantity per inflorescence: About 35; imbricate. Length: About 2.5 mm. Width: About 2 mm. Shape: Elliptic. Apex: Acute. Base: Truncate. Margin: Entire. Texture, upper and lower surfaces: Smooth, glabrous. Color, upper surface: 146B. Color, lower surface: 146A.

*Peduncle.*—Strength: Very strong; wiry. Aspect: Upright to slightly outward. Length, terminal inflorescence: About 3.7 cm. Length, second inflorescence: About 3.4 cm. Diameter: About 1 mm. Texture: Smooth, glabrous. Color: 144A.

*Reproductive organs.*—Androecium: Only on disc florets. Stamen quantity per floret: Five. Anther length: About 1 mm. Anther shape: Oval. Anther color: 21A.

Amount of pollen: Scarce. Pollen color: 17B. Gynoecium: Present on ray and disc florets. Pistil quantity per floret: One. Pistil length: About 4 mm. Stigma shape: Two-parted. Stigma color: 15A. Style length: About 2.5 mm. Style color: 1C. Ovary color: 145D.

*Seed/fruit.*—Seed and fruit production has not been observed.

Disease/pest resistance: Resistance to pathogens and pests common to *Argyranthemums* has not been observed on plants grown under commercial conditions.

Temperature/weather tolerance: Plants of the new *Argyranthemum* have been observed to be tolerant to rain, wind and to temperatures from 0° C. to 36° C.

It is claimed:

1. A new and distinct cultivar of *Argyranthemum* plant named 'Argywhimi', as illustrated and described.

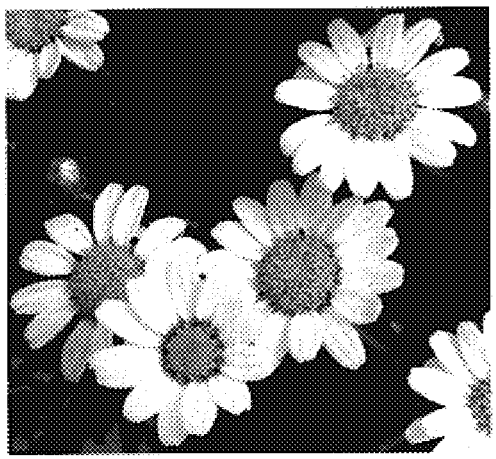
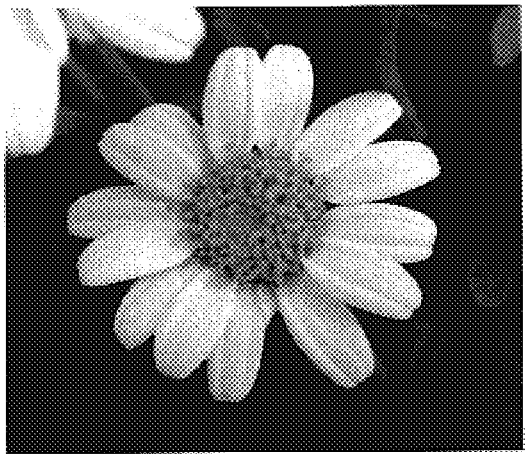
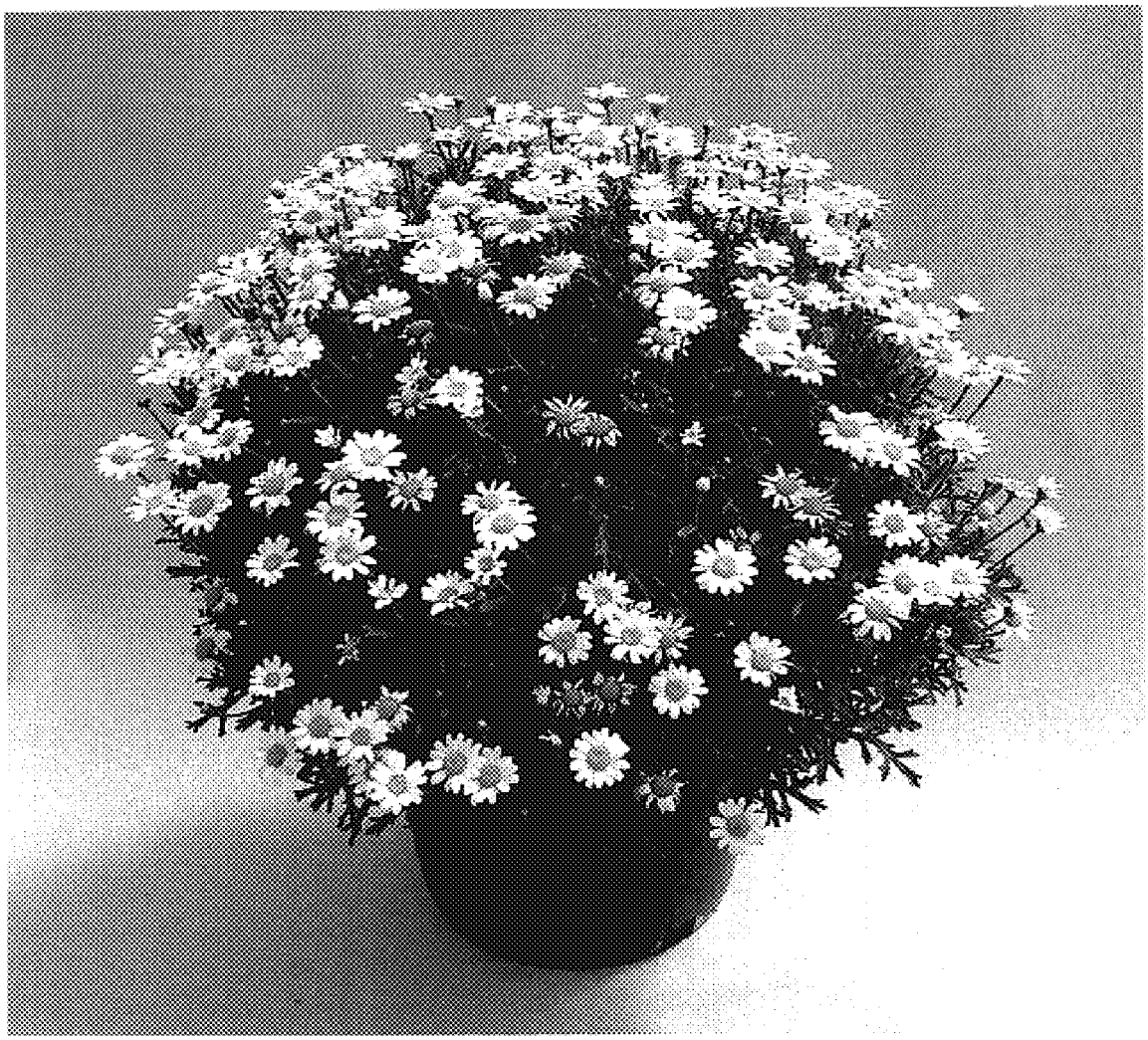

* * * * *